United States Patent
Elia et al.

(10) Patent No.: US 10,413,688 B2
(45) Date of Patent: Sep. 17, 2019

(54) SMART ETT VENTILATION ATTACHMENT AND METHOD OF USE

(71) Applicant: ART Healthcare Ltd., Natania (IL)

(72) Inventors: Liron Elia, Kiryat-Ata (IL); Gavriel J. Iddan, Haifa (IL)

(73) Assignee: ART Healthcare, Ltd., Natania (IL)

( * ) Notice: Subject to any disclaimer, the term of this patent is extended or adjusted under 35 U.S.C. 154(b) by 0 days.

(21) Appl. No.: 15/279,525

(22) Filed: Sep. 29, 2016

(65) Prior Publication Data
US 2017/0319804 A1 Nov. 9, 2017

Related U.S. Application Data

(60) Provisional application No. 62/333,625, filed on May 9, 2016.

(51) Int. Cl.
*A61M 16/04* (2006.01)
*A61M 16/00* (2006.01)
(Continued)

(52) U.S. Cl.
CPC .... *A61M 16/0463* (2013.01); *A61M 16/0003* (2014.02); *A61M 16/04* (2013.01);
(Continued)

(58) Field of Classification Search
CPC .............. A61M 16/00; A61M 16/0463; A61M 16/0003; A61M 16/201; A61M 16/04;
(Continued)

(56) References Cited

U.S. PATENT DOCUMENTS 4,967,759 A * 11/1990 Teves ............... A61B 7/023
600/528
5,313,939 A 5/1994 Gonzalez
(Continued)

FOREIGN PATENT DOCUMENTS

WO  WO 2007/130579  11/2007
WO  WO 2012/051541  4/2012
(Continued)

OTHER PUBLICATIONS

Communication Relating to the Partial International Search dated Jan. 26, 2017 From the International Searching Authority Re. Application No. PCT/IL2016/051070. (6 Pages).
(Continued)

*Primary Examiner* — Colin W Stuart

(57) ABSTRACT

An add-on device and method for an Endo-Tracheal Tube (ETT), the add-on device including a lengthy body having a major arc-shaped cross section sized and shaped to tightly fit over an ETT, at least one longitudinal cavity passing along the lengthy body, including a distal suction cavity ending with a suction inlet at a distal end of the lengthy body; and a distal suction outlet channel extending from a proximal end of the lengthy body, the channel is a continuous extension of the distal suction cavity and configured to provide suction to the distal suction cavity. The add-on device senses moisture at a distal end of the add-on device, and in case of detection of excessive wetness, provides suction to the distal end of the device through a cavity passing along the device, the suction is provided via a suction outlet channel extending from a proximal end of the device.

33 Claims, 9 Drawing Sheets

(51) Int. Cl.
*A61M 16/20* (2006.01)
*A61M 16/16* (2006.01)

(52) U.S. Cl.
CPC .... *A61M 16/0402* (2014.02); *A61M 16/0475* (2014.02); *A61M 16/0477* (2014.02); *A61M 16/0484* (2014.02); *A61M 16/201* (2014.02); *A61M 16/0431* (2014.02); *A61M 16/0479* (2014.02); *A61M 16/161* (2014.02); *A61M 2016/0413* (2013.01); *A61M 2205/07* (2013.01); *A61M 2205/15* (2013.01); *A61M 2230/432* (2013.01)

(58) Field of Classification Search
CPC .......... A61M 16/0402; A61M 16/0427; A61M 16/0431; A61M 16/0447; A61M 16/0461; A61M 16/0465; A61M 16/0475; A61M 16/0477; A61M 16/0479; A61M 16/0484; A61M 16/0486; A61M 2016/0413; A61M 25/00; A61M 25/0026; A61M 25/0071; A61M 2025/0004; A61M 2025/0024; A61M 2025/091; A61M 2039/00; A61M 2039/09; A61M 2202/007; A61M 2202/0014; A61M 1/00; A61M 1/0023; A61M 1/0025; A61M 1/0031; A61M 1/0035; A61M 1/0058; A61M 39/00; A61M 2039/0009; A61M 2202/0007
USPC .............................................. 128/207.14–18
See application file for complete search history.

(56) References Cited

U.S. PATENT DOCUMENTS

| 5,370,656 | A | * | 12/1994 | Shevel | A61F 13/36 206/440 |
| 6,460,540 | B1 | | 10/2002 | Klepper | |
| 7,278,429 | B2 | * | 10/2007 | Johnson | A61M 16/04 128/207.14 |
| 8,939,951 | B1 | * | 1/2015 | Getsay | A61M 1/008 604/319 |
| 2008/0011304 | A1 | * | 1/2008 | Stewart | A61M 16/04 128/207.15 |
| 2009/0229615 | A1 | | 9/2009 | Stenzler et al. | |
| 2010/0030133 | A1 | * | 2/2010 | Elia | A61B 5/037 604/28 |
| 2010/0065062 | A1 | * | 3/2010 | Rajan | A61M 16/0488 128/207.14 |
| 2010/0163023 | A1 | | 7/2010 | Singh | |
| 2010/0180737 | A1 | | 7/2010 | Klepper | |
| 2011/0237896 | A1 | * | 9/2011 | Black | A61M 16/0463 600/188 |
| 2012/0272955 | A1 | | 11/2012 | Cool et al. | |
| 2013/0014761 | A1 | * | 1/2013 | Elia | A61M 16/04 128/207.15 |
| 2014/0109903 | A1 | * | 4/2014 | Chaudhry | A61M 16/0488 128/202.15 |
| 2014/0224247 | A1 | * | 8/2014 | Tan | A61M 16/16 128/203.14 |
| 2014/0366874 | A1 | * | 12/2014 | Deutsch | A61M 16/044 128/202.13 |
| 2015/0190597 | A1 | * | 7/2015 | Zachar | A61C 17/04 128/200.14 |
| 2015/0258292 | A1 | | 9/2015 | Stottler et al. | |
| 2016/0038014 | A1 | * | 2/2016 | Molnar | A61M 16/0003 600/109 |
| 2016/0045698 | A1 | * | 2/2016 | Chaturvedi | A61M 16/0463 128/204.21 |
| 2016/0325063 | A1 | * | 11/2016 | Khosrowshahi | A61M 16/0463 |

FOREIGN PATENT DOCUMENTS

| WO | WO 2016/022759 | 2/2016 |
| WO | WO 2017/195186 | 11/2017 |

OTHER PUBLICATIONS

International Search Report and the Written Opinion dated May 10, 2017 From the International Searching Authority Re. Application No. PCT/IL2016/051070. (18 Pages).

International Preliminary Report on Patentability dated Nov. 22, 2018 From the International Bureau of WIPO Re. Application No. PCT/IL2016/051070. (11 Pages).

* cited by examiner

SMART ETT VENTILATION ATTACHMENT AND METHOD OF USE

RELATED APPLICATION

This application claims the benefit of priority under 35 USC § 119(e) of U.S. Provisional Patent Application No. 62/333,625 filed on 9 May 2016, the contents of which are incorporated herein by reference in their entirety.

FIELD AND BACKGROUND OF THE INVENTION

When a patient has difficulty breathing autonomously, it is a common practice to insert an external tubular tracheal ventilation tube, also known as Endo-Tracheal Tube (ETT). An ETT provides fresh air by a forced ventilation pump, and ejects air saturated with $CO_2$. Thus, the breathing operation is performed instead of the patient and the needed oxygen is provided to the patient's organs.

During the forced ventilation process, excessive fluids and secretion are usually aggregated in the mouth and trachea of the patient. Some of the known ETTs include a "balloon", i.e. an inflatable section, intended for blocking the fluids from entering further to the trachea and lungs.

SUMMARY OF THE INVENTION

According to an aspect of some embodiments of the present invention there is provided an add-on device for an Endo-Tracheal Tube (ETT), the add-on device including a lengthy body having a major arc-shaped cross section sized and shaped to tightly fit over an ETT, at least one longitudinal cavity passing along the lengthy body, comprising a distal suction cavity ending with a suction inlet at a distal end of the lengthy body, and a distal suction outlet channel extending from a proximal end of the lengthy body, the channel is a continuous extension of the distal suction cavity and configured to provide suction to the distal suction cavity.

In some embodiments of the present invention, the device includes a moisture sensor for detection of liquid at the distal end of the lengthy body and at least one sensor data channel going through at least one of the longitudinal cavities towards the proximal end of the device.

In some embodiments of the present invention, the device includes a mouth suction tube extending from an external surface of the lengthy body at a location corresponding to a patient's mouth, wherein the at least one longitudinal cavity further comprising a mouth suction cavity continuous to the mouth suction tube, and a mouth suction outlet channel extending from the proximal end of the lengthy body, the mouth suction outlet channel is a continuous extension of the mouth suction cavity and configured to provide suction to the mouth suction cavity.

In some embodiments of the present invention, the device includes a moisture sensor at the distal end of the mouth tube and at least one sensor data channel going through at least one of the longitudinal cavities towards the proximal end of the device.

In some embodiments of the present invention, the mouth suction tube is connected to the lengthy body by an axis perpendicular to the lengthy body at the connection point, the mouth suction tube tiltable about the axis to adjust the position of the mouth suction tube.

In some embodiments of the present invention, the device includes a liquid outlet at an external surface of the lengthy body at a location corresponding to a patient's mouth, wherein the at least one longitudinal cavity further comprising a liquid channel cavity continuous to the liquid outlet, and a liquid channel extending from the proximal end of the lengthy body, the liquid channel is a continuous extension of the liquid channel cavity and configured to provide liquid to the liquid outlet.

In some embodiments of the present invention, the liquid outlet is connected to the lengthy body by an axis perpendicular to the lengthy body at the connection point, the liquid outlet tiltable about the axis to adjust the position of the liquid outlet.

In some embodiments of the present invention, the device includes at a distal end of the lengthy body a recess formed in an internal wall of the lengthy body, configured to prevent clogging of the suction inlet.

In some embodiments of the present invention, the device includes an inlet at the distal end of the lengthy body and a CO2 sampling pipe continuous to the inlet going through at least one of the longitudinal cavities towards the proximal end of the device.

In some embodiments of the present invention, the device includes an outlet bundle of outlet channels including the distal suction outlet channel, the outlet bundle extending from the proximal end of the lengthy body.

In some embodiments of the present invention, the at least one longitudinal cavity pass in a thickness of the lengthy body.

According to an aspect of some embodiments of the present invention there is provided an add-on device for an Endo-Tracheal Tube (ETT), the add-on device including a liquid outlet at a location corresponding to a patient's mouth, a moisture sensor at a location corresponding to a patient's mouth, and at least one longitudinal cavity passing along the device and including a liquid channel cavity continuous to the liquid outlet, and a moisture sensor data channel, the liquid channel and data channel going through the at least one longitudinal cavities towards the proximal end of the device, wherein the liquid channel is adapted to guide liquid from a liquid source to the liquid outlet according to data transmitted through the moisture sensor data channel.

According to an aspect of some embodiments of the present invention there is provided a system including an add-on device for an Endo-Tracheal Tube (ETT), the add-on device including at least one longitudinal cavity passing along the device, comprising a distal suction cavity ending with a suction inlet at a distal end of the device, and a distal suction outlet channel extending from a proximal end of the device, the channel is a continuous extension of the distal suction cavity and configured to provide suction to the distal suction cavity, and a hub for operating the add-on device, the hub comprises a controller configured to control suction supply to the distal suction outlet channel according to moisture sensor data.

In some embodiments of the present invention, the device includes a lengthy body having a major arc-shaped cross-section.

In some embodiments of the present invention, the controller is configured to detect excessive wetness based on moisture sensor data, and when excessive wetness is detected, activate suction through the distal suction outlet channel.

In some embodiments of the present invention, the device includes a mouth suction tube extending from an external surface of the device at a location corresponding to a patient's mouth, wherein the at least one longitudinal cavity further comprising a mouth suction cavity continuous to the mouth suction tube, and a mouth suction outlet channel extending from the proximal end of the device, the mouth suction outlet channel is a continuous extension of the mouth suction cavity and configured to provide suction to the mouth suction cavity, wherein the controller is configured to switch a selection valve to select between the distal suction outlet channel and the mouth suction outlet channel, and switch a pinch valve to control suction supply to the selected suction outlet channel.

In some embodiments of the present invention, the device includes a liquid outlet at an external surface of the device at a location corresponding to a patient's mouth, wherein the at least one longitudinal cavity further comprising a liquid channel cavity continuous to the liquid outlet, and a liquid channel extending from the proximal end of the device, the liquid channel is a continuous extension of the liquid channel cavity and configured to provide liquid to the liquid outlet, wherein the controller is configured to activate a liquid source to provide liquid via the liquid channel.

In some embodiments of the present invention, the hub includes an air compressor, wherein the controller is configured to activate the air compressor to push liquid forcefully through the liquid channel.

In some embodiments of the present invention, the device includes an inlet at the distal end of the device and a $CO_2$ sampling pipe continuous to the inlet going through at least one of the longitudinal cavities towards the proximal end of the device, and wherein the hub comprises a $CO_2$ level sensor configured to receive a sample of air via the $CO_2$ sampling pipe and to measure $CO_2$ level in the sample.

In some embodiments of the present invention, the controller is configured to detect air leakage based on the measured $CO_2$ level.

In some embodiments of the present invention, the controller is configured to control inflation of an inflatable section of the ETT based on sensor data.

According to an aspect of some embodiments of the present invention there is provided a method for controlling an add-on device for an Endo-Tracheal Tube (ETT), the method including, when the add-on device is installed on the ETT, sensing moisture at a distal end of the add-on device, and in case of detection of excessive wetness, provide suction to the distal end of the device through a cavity passing along the device, the suction is provided via a suction outlet channel extending from a proximal end of the device.

In yet another embodiments the said suction channels, the fluid channel as well as the moisture sensors are embedded in the ETT tube directly and connected to the hub by said cable.

In yet another embodiment a liquid absorbing media such as a sponge is replacing the balloon.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
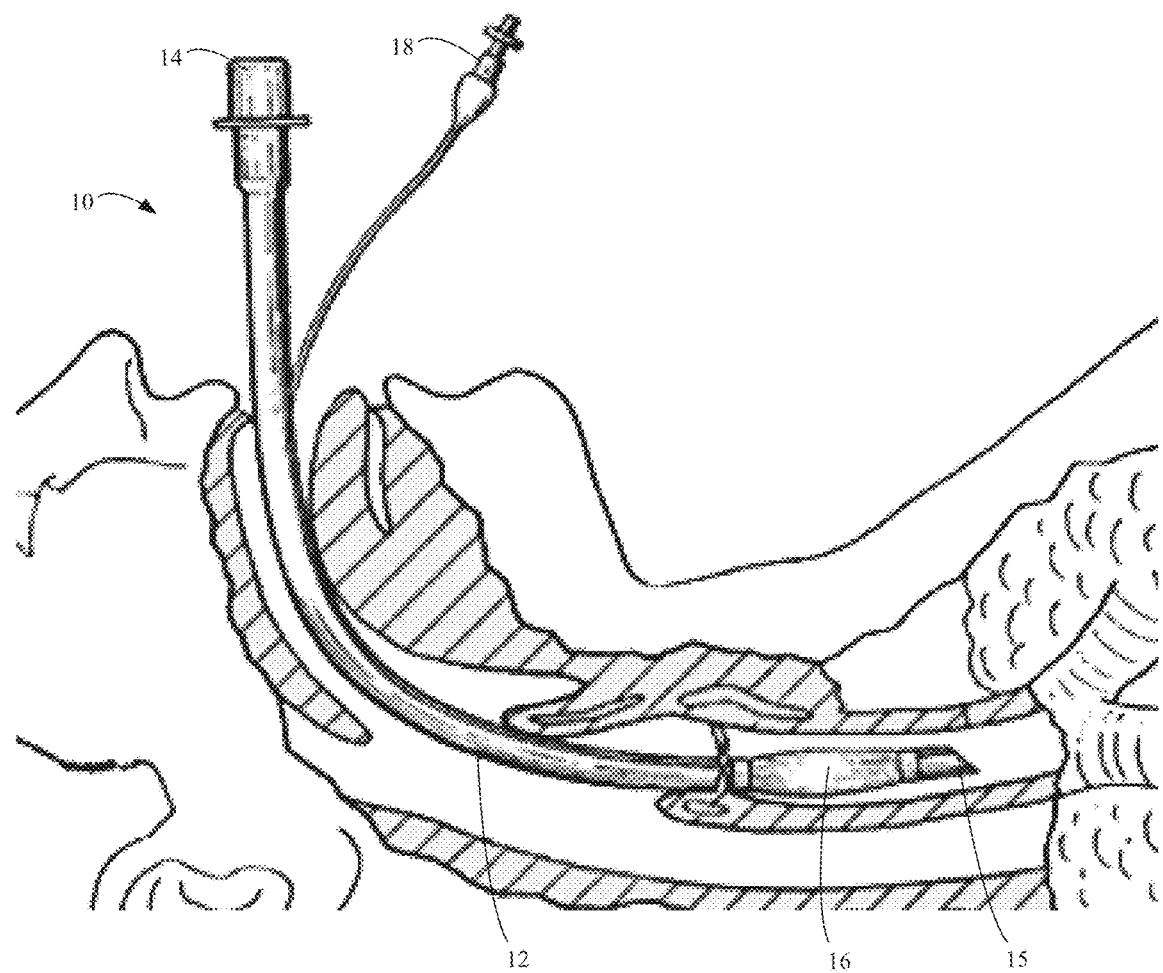
FIG. 1 is a schematic illustration of an ETT as known in the art.

The existing ETT ventilation tubes have some shortcomings. Secretion may be accumulated on the balloon and eventually may get into the lungs. Saliva and mucus may be accumulated in the mouth, and in some cases, for example when the patient doesn't eat and/or drink through the mouth, excessive dryness may be formed, which may cause infections.

In to some embodiments of the present invention a ventilation enhancement device is provided, which may be an add-on device for installation on the ETT with minimal or no interruption to the ventilation process, or may be integral with the ETT. The ventilation enhancement device according to some embodiments of the present invention enables removal of excessive fluids and secretion from the trachea and mouth during the ventilation by the ETT with no need to replace a currently installed ETT.

The provided add-on device may include a wrap with a c-shaped cross-section and/or a longitudinal slit, which may simply be snapped upon the ETT without requiring any additional installation steps.

The enhancement device may remove the fluids from the trachea by a suction inlet in the vicinity of the device's end. The fluids accumulated in the mouth may be removed by the enhancement device by a suction inlet on the wrap in a location corresponding to the patient's mouth. In order to avoid dryness in the mouth, fluid may be sprayed, periodically and/or when needed, out of an opening in the external surface of the wrap, in a location corresponding to the patient's mouth.

According to some embodiments of the present invention, suction may be provided to the enhancement device by a controller, according to signals received from dedicated sensors located at the vicinity of the suction inlets. Excessive fluids and secretion in the trachea and mouth may be detected, for example, by impedance measurements.

In some embodiments of the present invention, the enhancement device may detect an unwanted gap between the trachea wall and the balloon of the ETT. Such gap may cause leakage of secretion into the lungs. The detection of an unwanted gap is done by detection of air leaking from the gap, by detection of $CO_2$ levels in the vicinity of the balloon. Detector signals may be provided to a controller, which may control the suction accordingly.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As mentioned herein, an enhancement device according to some embodiments of the present invention may be installed on or be integral with a typical ETT, for sensing existence of excessive secretion and/or dryness in a patient's trachea lumen and/or a mouth, and for providing suction and/or wetness as needed.

Reference is now made to FIG. 1, which is a schematic illustration of an ETT 10 as known in the art. ETT 10 includes a ventilation tube 12, a ventilation inlet 14 and a ventilation outlet 15, which is configured to be inserted into the trachea. Additionally, ETT 10 includes an inflatable section 16 and an inflation tube 18. Once ETT 10 in inserted via the mouth or nose of the patient, and ventilation outlet 15 is at a desirable location within the trachea, inflatable section 16 may be inflated by tube 18 until it occupies the entire width of the trachea, within a permitted inflation pressure range, in order to prevent invasion of secretion further into the trachea and the lungs. However, as mentioned above, the obstruction of the trachea by inflatable section 16 is not always sufficient and secretion may still penetrate to the lungs through gaps between inflatable section 16 and the trachea walls.

Figure 2:
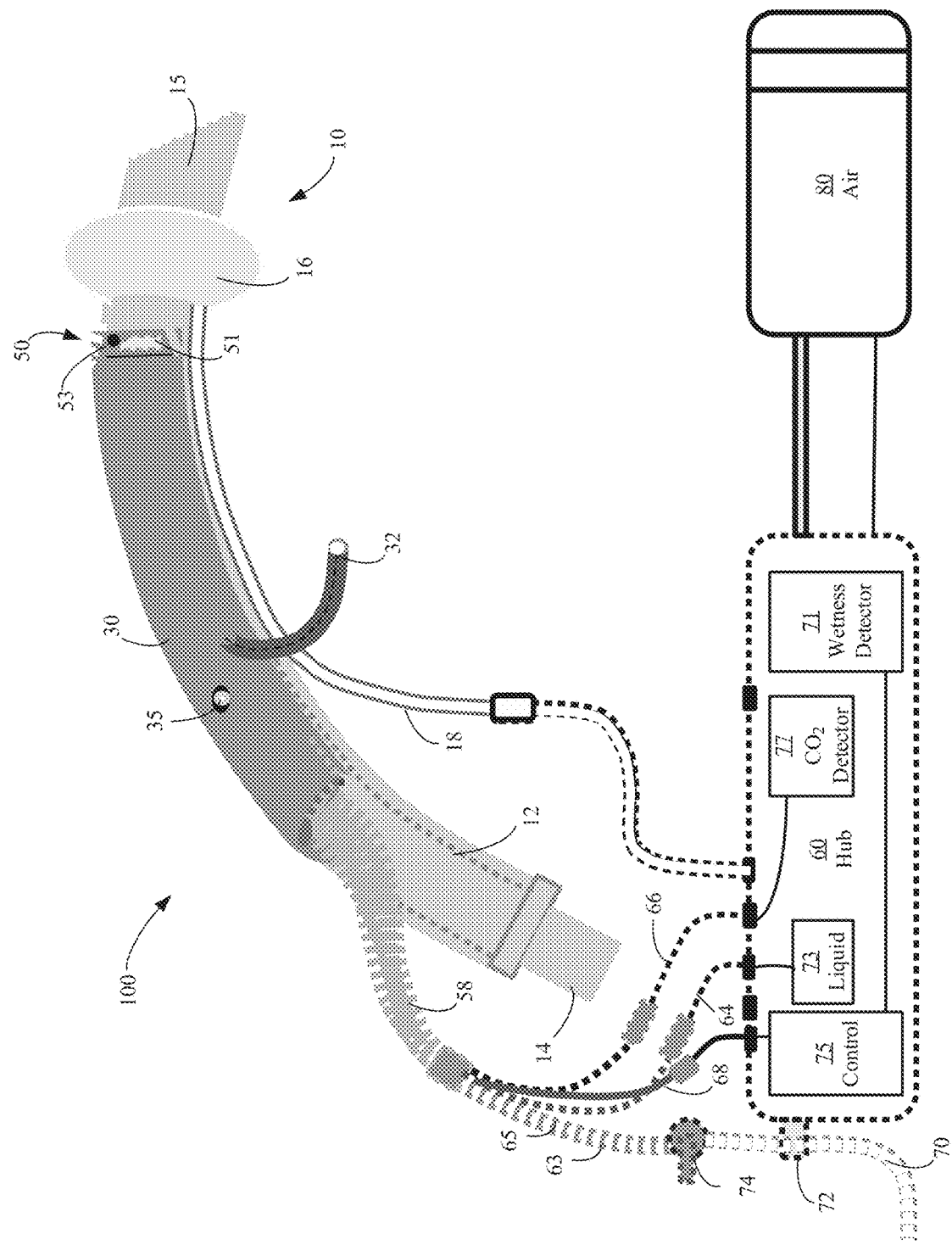
FIG. 2 is a schematic illustration of a ventilation enhancement device installed on or integral with an ETT, according to some embodiments of the present invention.

Reference is now made to FIG. 2, which is a schematic illustration of an enhancement device 100 installed on an ETT 10, according to some embodiments of the present invention. Device 100 includes a wrap 30, which may be made, for example, of a biocompatible polymer approved by regulation such as polyurethane, for wrapping ETT 10. Wrap 30 may be installed on ETT 10, for example, by snap-fitting, clipping, or sliding of wrap 30 onto ETT 10, or by any other suitable attachment method. In some embodiments, wrap 30 is tunnel-shaped, with a c-shaped or a major circle-arc cross section (as shown, for example, in FIGS. 5 and 7A-7B). In other embodiments, wrap 30 may have a closed circle cross-section.

In some embodiments of the present invention, device 100 is integral with an ETT device. For example, device 100 illustrated in FIG. 2 may be integral with ETT 10 and constitute an enhanced ETT device including the features of the ETT and of device 100 described herein, for sensing existence of excessive secretion and/or dryness in a patient's trachea lumen and/or a mouth, and for providing suction and/or wetness as needed. Accordingly, it will be appreciated that add-on device 100 described throughout the present invention is in some embodiments integral with an ETT device and constitutes an enhanced ETT device.

At a distal end of wrap 30, device 100 includes a trachea suction port 50. When installed on ETT 10, trachea suction port may be located just before balloon 16, in order to remove secretion, such as mucus, saliva or pus, before it reaches further in the trachea. Trachea suction port 50 may include, for example, one or more trachea suction inlets 51 for removal of secretion and/or mucus from the trachea, $CO_2$ inlet for detection of $CO_2$ in the trachea (shown, for example, in FIG. 5), and a moisture sensor 53 for detecting of secretion fluid. In some embodiments of the present invention, the outer surface of the distal end of device wrap 30 is smooth and/or tapered, thus facilitating easy insertion of wrap 30 into the trachea.

Device 100 may also include a mouth pipe 32 for removal of secretion and/or mucus from the mouth, which may also include a moisture sensor for detecting of secretion fluid. In some embodiments, device 100 may include a liquid outlet 35, for providing liquid, possibly disinfecting fluid, into the mouth in order to avoid excessive dryness and/or infection, for example by spraying the fluid into the mouth. For example, the spray liquid can range from water to mouthwash or other medicated fluid. In some embodiments, device 100 may include one or more additional sensors at the distal end of wrap 30 or in the vicinity of mouth tube 32, such as, for example, a sensor of temperature, manometry, light, acidity level, sound, and/or any other suitable sensor.

At a proximal end, device 100 may include an outlet bundle 58, including secretion suction tubes 63 and 65, a liquid channel 64, a $CO_2$ detection channel 66, sensor data wires 68, and/or any other suitable transmission pipe from and/or into device 100. Suction tubes 63 and 65, liquid channel 64, $CO_2$ channel 66 and or sensor data wires 68 may be controlled by a hub 60, which may include a controller circuit 75 and/or a processor 79, described in more detail with reference to FIG. 4.

Figure 4:
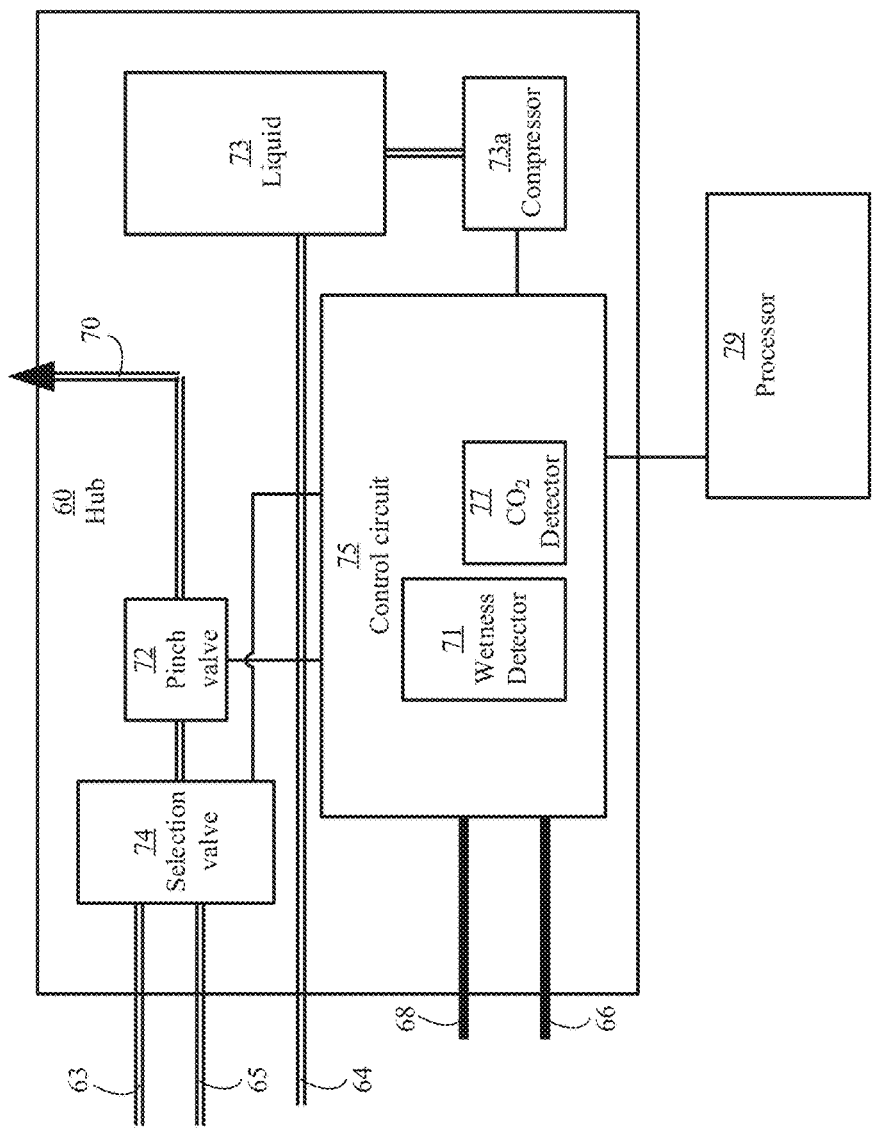
FIG. 4 is a schematic illustration of a hub according to some embodiments of the present invention.

FIG. 4 is a schematic illustration of hub 60 according to some embodiments of the present invention. Hub 60 may receive sensor data via sensor data wires 68 and/or $CO_2$ detection data, and control based on the received data the liquid supply and/or the secretion suction. In some embodiments, hub 60 may control inflation of balloon 16 via inflation tube 18, with air from an air source 80, as shown in FIG. 2.

For example, typical impedance values detected by the moisture sensors may range from more than 1000 Ohm for a dry environment to about 100 Ohm for wet environment, or some intermediate impedance value.

Figure 5:
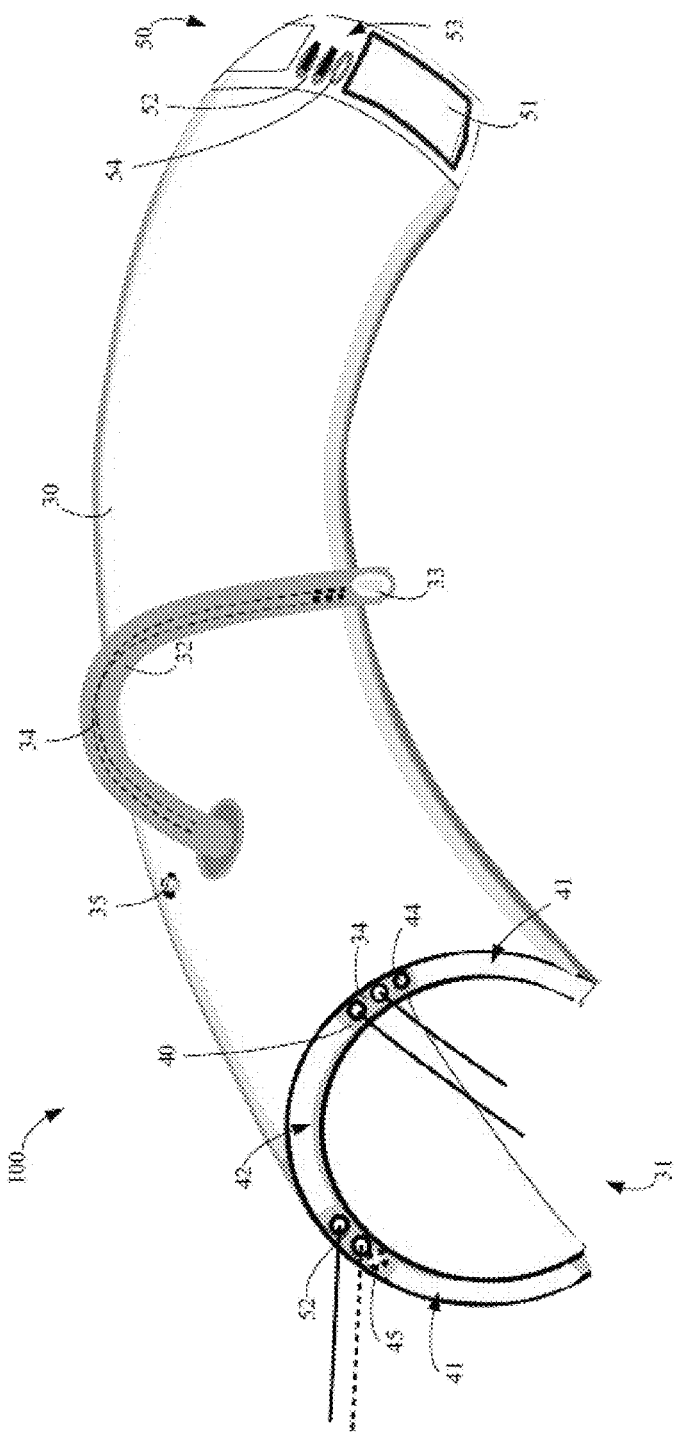
FIG. 5 is a schematic more detailed illustration of an add-on device and an exemplary cross-section of a proximal end of a wrap according to some embodiments of the present invention.

Suction tubes 63 and 65 may include a distal secretion suction tube and a mouth secretion suction tube, as shown in more detail in FIG. 5. Hub 60 may control the secretion suction operation by a pinch valve 72. Pinch valve 72 may control the flow in suction tubes 63 and 65 or in a main suction tube 70, from which suction tubes 63 and 65 may split. Suction tubes 63 and 65 may be controlled separately by hub 60, for example by a selection valve 74. Suction pressure may be regulated by an available vacuum source, from which main suction tube 70 may provide the vacuum.

Figure 3:
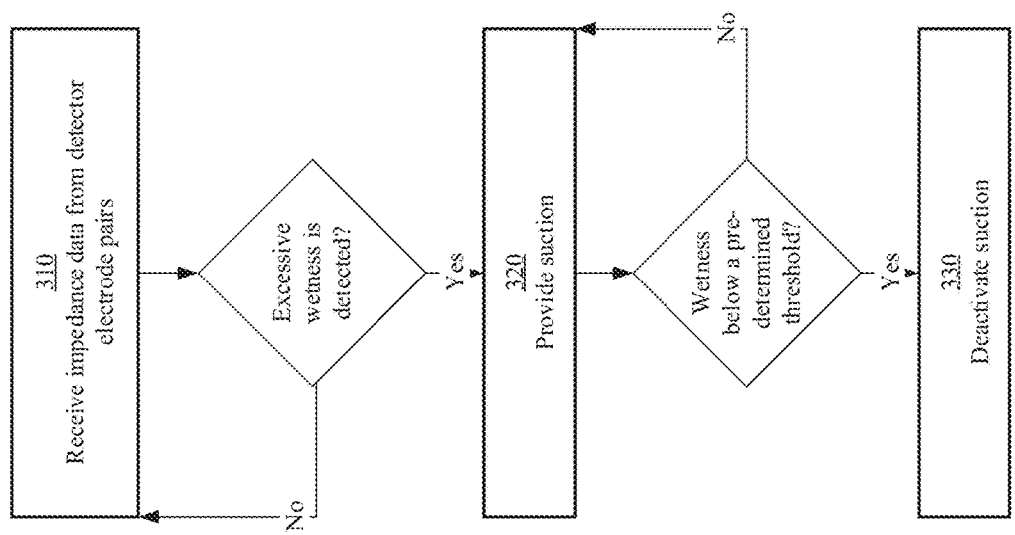
FIG. 3 is a schematic flowchart illustrating a method for controlling a ventilation enhancement device according to some embodiments of the present invention.

During operation, wrap 30 is installed over ETT 10 and placed within a patient's body lumen, for example along the trachea through the mouth or nose. Reference is now made to FIG. 3, which is a schematic flowchart illustrating a method 300 for controlling an enhancement device 100 according to some embodiments of the present invention. As indicated in block 310, controller 75 may activate a moisture detector 71, which may receive, for example, impedance data from detector electrode pairs 34 and 52 via wires 68. As indicated in block 320, in case excessive wetness is detected at electrode mouth pair 34 and/or distal pair 52, a corresponding signal may be sent to controller 75/processor 79, which may activate suction by opening pinch valve 72, and/or may operate selection valve 74 to activate suction from the mouth, from the trachea, or both. Controller 75/processor 79 may detect excessive wetness when it exceeds a pre-determined threshold. As indicated in block 330, the suction may be activated as long as a predetermined condition is fulfilled, for example, for a pre-determined period of time, or until the sensor data indicates normal wetness, or wetness below a pre-determined threshold, in which case controller 75 may deactivate the suction.

Controller circuit 75 may be controlled by processor 79, which may be external or internal to hub 60.

In order to prevent excessive dryness in the mouth, controller 75 may activate a liquid source 73 to provide liquid to liquid outlet 35 via liquid channel 64. Liquid source 73 may be activated in a predetermined time intervals, manually and/or according to sensor data. The liquid provided by source 73 may include water and/or an oral care solution, to avoid mouth infections. In some embodiments, hub 60 includes an air compressor 73a. Controller 75 may activate air compressor 73a to push air forcefully into liquid source 73, which as result pushes liquid forcefully through liquid channel 64, and create spray effect out of liquid outlet 35.

In some embodiments of the present invention, device 100 may detect air leakage from balloon 16. Hub 60 may include a $CO_2$ level sensor 77. $CO_2$ sensor 77 may receive a sample of air from the vicinity of balloon 16, via $CO_2$ tube 66, and measure the $CO_2$ level in the sample. As described below with reference to FIG. 5, trachea suction port 50 may include $CO_2$ inlet 54, through which the air sample is taken. From the measured $CO_2$ levels, controller 75 may detect an unwanted gap between the trachea wall and balloon 16, by deducing when air is leaked from balloon 16.

Reference is now made to FIG. 5, which is a schematic more detailed illustration of add-on device 100 and an exemplary cross-section of a proximal end of wrap 30 according to some embodiments of the present invention. Wrap 30 may include a longitudinal opening 31, making the cross-section of wrap 30 c-shaped and/or major arc-shaped and facilitating installation of wrap 30 on ETT 10. Trachea suction port 50 may include, for example, one or more trachea suction inlets 51 for removal of secretion and/or mucus from the trachea, and/or $CO_2$ inlet 54 for detection of $CO_2$ from the trachea by taking a sample of the air in proximity to balloon 16.

In some embodiments of the present invention, additional or alternative suction port(s) 50 is located along wrap 30 to prevent liquid from entering through longitudinal opening 31. In some embodiments, wrap 30 includes along longitudinal opening 31 a liquid absorbing and/or expanding material, such as a sponge, as described in PCT publication WO 2011/117854 A3. Moisture sensor 53 may include detector electrode pair 52. Mouth pipe 32 may include a suction opening 33 for removal of secretion and/or mucus from the mouth and a moisture sensor for detecting of secretion fluid, including a detector electrode pair 34.

Wrap 30 may include a core 40 of thickness d, i.e. the thickness of wrap 30 between the external and internal perimeters of wrap 30. Within core 40 passes a plurality of longitudinal suction cavities, pipes and/or detector wires passing along wrap 30. As mentioned herein, the various suction cavities may accumulate and remove secretion and/or mucus from the mouth and/or from the trachea. Other pipes may be used for transmission of air sampling out of the trachea, transmission of liquids to the mouth and/or transmission of other suitable materials out of or into the trachea and/or the mouth as needed. In some embodiments, wrap 30 may include, within core 40, secretion suction cavities 41 and 42 for the trachea and mouth, respectively, a $CO_2$ sampling pipe 44, liquid pipe 45, detector electrode pairs 34 and 52, and/or any other suitable pipes and/or wires.

Detector electrode pairs 34 and 52 may be used for impedance measurements in the trachea and/or mouth, for example for detection of moisture levels in the trachea and/or mouth and/or in order to identify secretion and/or excessive dryness. Based on the impedance measurements, a controller may determine whether to activate suction via cavities 41 and 42 and/or transmission of liquids via liquid pipe 45 to liquid outlet 35.

Figure 6:
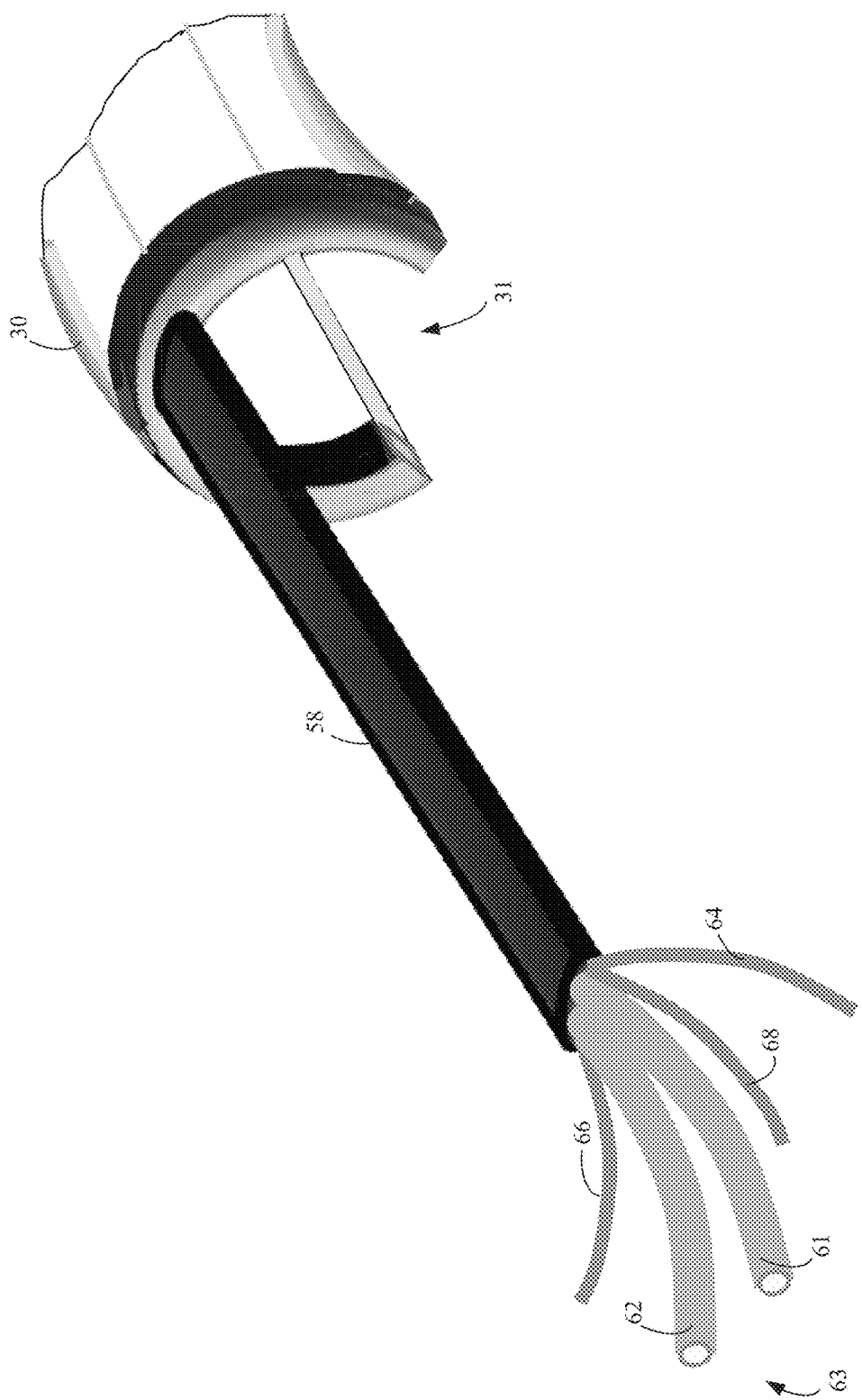
FIG. 6 is a schematic more detailed illustration of an outlet bundle, according to some embodiments of the present invention.

Reference is now made to FIG. 6, which is a schematic more detailed illustration of outlet bundle 58, according to some embodiments of the present invention. Outlet bundle 58 may extend out from the proximal end of wrap 30 and guide the various suction and data channels out of the patient's mouth, to external sources such as a vacuum source and/or hub 60. An external trachea suction tube 61 and a mouth suction tube 62 may provide suction to cavities 41 and 42 shown in FIG. 5, respectively, for example from a vacuum source. An external liquid channel 64 may provide liquid to liquid pipe 45 shown in FIG. 5. An external $CO_2$ channel 66 may eject air sample from $CO_2$ sampling pipe 44 shown in FIG. 5. Data wires 68 may transmit sensor data from electrode pairs 34 and 52 shown in FIG. 5.

Figure 7A:
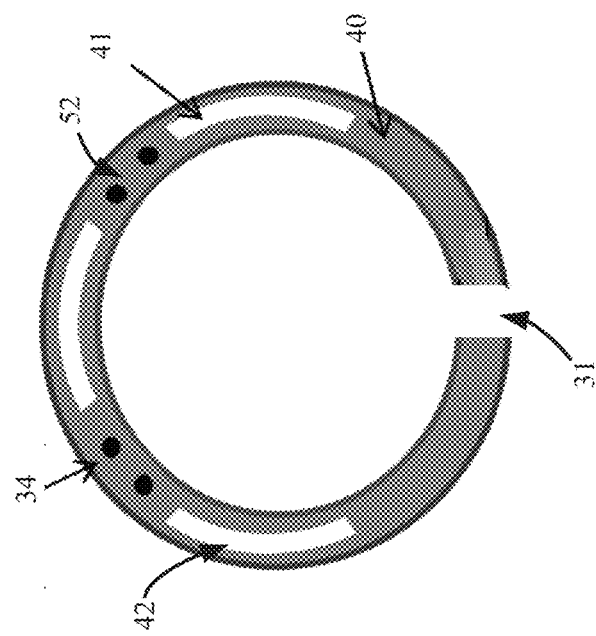
FIGS. 7A and 7B are schematic cross-sectional illustrations of exemplary proximal and distal ends of a wrap according to some embodiments of the present invention.
Figure 7B:
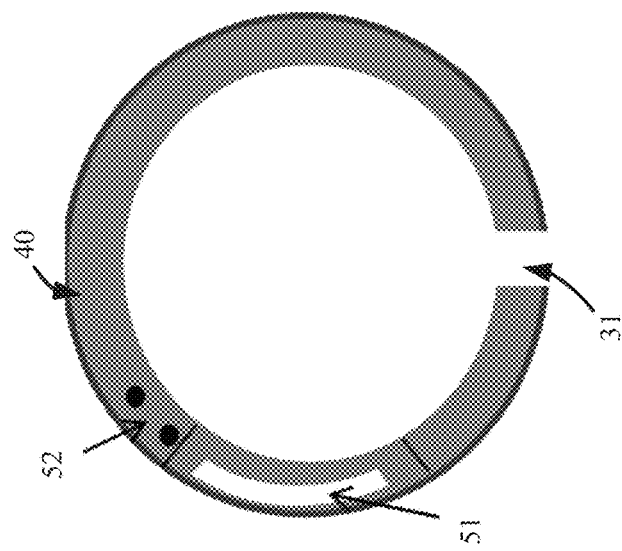

Reference is now made to FIGS. 7A and 7B, which are schematic cross-sectional illustrations of exemplary proximal and distal ends 30a and 30b of wrap 30, respectively, according to some embodiments of the present invention. As described above, wrap 30 may have a c-shaped or a major circle-arc cross-section, including a core 40 in which a plurality of detector electrode pairs 34 and 52 and suction cavities 41 and 42 may be formed, possibly along with any additional suitable pipes and/or channels. A longitudinal opening 31 may facilitate the mounting of wrap 30 upon ETT 10. Proximal end 30a is located before mouth pipe 32, and therefore, as shown in FIG. 7A, assembles both mouth and distal detector electrode pairs 34 and 52, and both mouth and distal suction cavities 42 and 41, as well as any additional pipes and channels, which may pass through wrap 30 and be guided out of the patient's mouth. Distal end 30b, as shown in FIG. 7B, may include trachea suction inlets 51 and the distal end of detector electrode pair 52, as well as any additional inlets such as, for example, a $CO_2$ sampling inlet.

Reference is now made to FIGS. 8A-8D, which are additional schematic views of add-on device 100, according to some embodiments of the present invention.

Figure 8A:
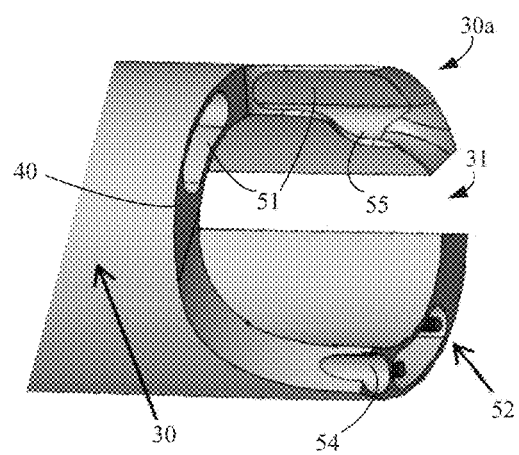
FIGS. 8A-8D are additional schematic views of an add-on device, according to some embodiments of the present invention.
Figure 8B:
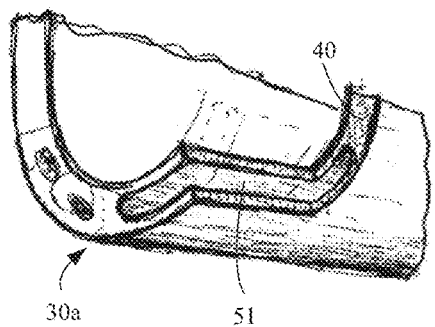

FIGS. 8A and 8B are more detailed illustrations of distal end 30a, according to some embodiments of the present invention. As shown in FIG. 8A, distal end 30a may include a recess 55. Recess 55 may be formed in distal end 30a, for example in an internal wall of wrap 30. When suction is provided through inlet 51, a wall of the trachea may collapse towards inlet 51. Recess 55 may provide air opening that may prevent clogging of inlet 51 by the collapsed trachea wall. Electrode pair 52 may be disposed within the core of thickness of a rim of distal end 30a. As shown in FIG. 8B, in some embodiments, recess 55 opens inlet 51 from the side, so that suction through inlet 51 is enabled even when distal end 30a is in close proximity to the trachea wall.

Figure 8C:
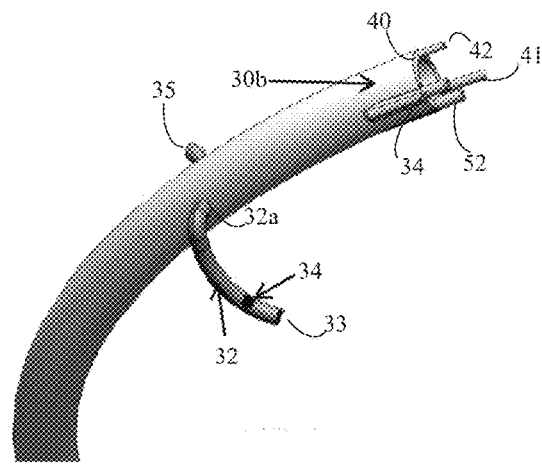
Figure 8D:
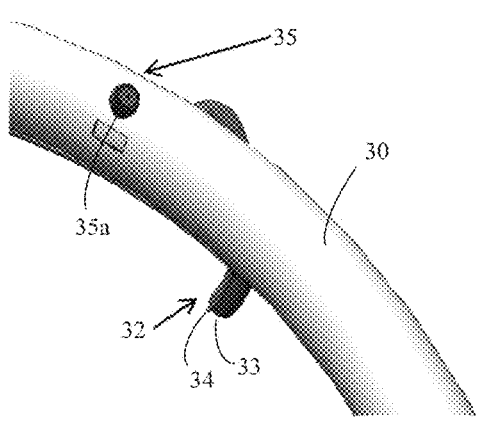

FIGS. 8C and 8D are more detailed illustrations of a portion of wrap 30 including mouth suction tube 32 and liquid outlet 35, according to some embodiments of the present invention, and a cross-section of wrap 30 at a location between bundle 58 and mouth suction tube 32, according to some embodiments of the present invention. In some embodiments of the present invention, mouth suction tube 32 and/or liquid outlet 35 are connected to wrap 30 by axes 32a and 35a, respectively, perpendicular to wrap 30. In some embodiments of the present invention, mouth suction tube 32 and/or liquid outlet 35 protrude from wrap 30 and curved toward their distal ends. Mouth suction tube 32 and/or liquid outlet 35 can be tilted about their respective axis. This way, the direction of tube 32 and/or outlet 35 may be adjusted in the patient's mouth.

As described herein, electrode pair 34 and/or one or more other sensors may be located on tube 32, proximately to or at opening 33. As described herein, sensor data channels including detector electrode pairs 34 and 52, and mouth and distal suction cavities 42 and 41, may pass within core 40 of wrap 30 towards bundle 58 and/or hub 60. In some embodiments, $CO_2$ sampling pipe 44, liquid pipe 45, and/or any other suitable pipes and/or wires, pass within core 40.

Figure 9B:
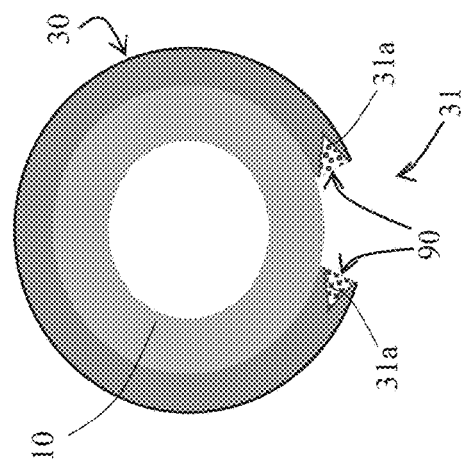
FIGS. 9A and 9B are schematic cross-sectional illustrations of an exemplary add-on device including a liquid absorbing material according to some embodiments of the present invention.
Figure 9A:
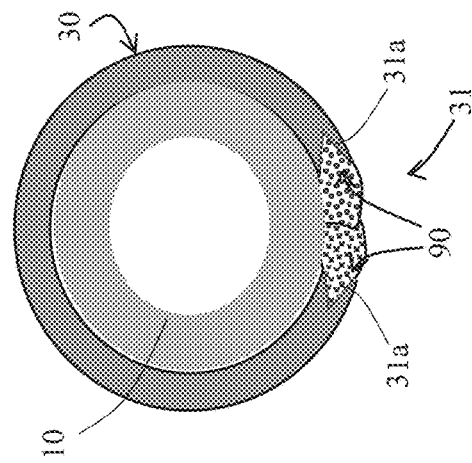

Reference is now made to FIGS. 9A and 9B, which are schematic cross-sectional illustrations of an exemplary wrap 30 including a liquid absorbing material 90 according to some embodiments of the present invention, before and after liquid absorbing, respectively. Wrap 30 may include along longitudinal opening 31 a liquid absorbing material 90, such as a sponge or foam, for example as described in PCT publication WO 2011/117854 A3. For example, material 90 may be laid out along two opposing sides of opening 31. In some embodiments, wrap 30 includes recesses 31a in two opposing sides of opening 31, in which material 30 is laid. Material 90 has an expanded state and an unexpanded state, shown in FIGS. 9B and 9A, respectively.

Material 90 takes the expanded state when absorbing liquid. Before insertion of wrap 30 into the trachea, as shown in FIG. 9A, material 90 is substantially dry and unexpanded, keeping opening 31 open and thus, for example, enabling snap-fitting, clipping, or sliding of wrap 30 onto ETT 10. After insertion of wrap 30 into the trachea, as shown in FIG. 9B, wrap 30 is in a moist environment and material 90 may absorb fluids and expand, filling opening 31. The expanded material 90 provides better grip of wrap 30 on ETT 10 and assists in preventing penetration of secretion into the lungs and/or between wrap 30 and ETT 10.

The methods as described above are used in the fabrication of integrated circuit chips.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An add-on device for an Endo-Tracheal Tube (ETT), the add-on device comprising:
   a lengthy body having a curvature, a major arc-shaped cross section and a longitudinal slit, the lengthy body sized and shaped for facilitating installation over an ETT while the ETT is located within a trachea of a ventilated patient,
   wherein the major arc-shaped cross section extends along a length of the lengthy body, from a distal end of the lengthy body to a proximal end of the lengthy body;
   a plurality of discrete longitudinal cavities each having an arc-shaped cross section passing along the lengthy body, comprising a suction cavity;
   a suction outlet channel extending from the proximal end of the lengthy body, the suction outlet channel is a continuous extension of the suction cavity and configured to provide suction to the suction cavity;
   at least one impedance sensor for detection of liquid, disposed at the distal end of the lengthy body;
   at least one sensor data channel from the at least one impedance sensor to the proximal end of the lengthy body, passing within a core of thickness of the major arc-shaped cross section, and spaced apart from the plurality of discrete longitudinal cavities; and
   a controller that receives data from the at least one impedance sensor and automatically activates suction of the suction outlet channel to create suction in the suction cavity when excessive wetness exceeding a pre-determined threshold is detected by the at least one impedance sensor.

2. The add-on device of claim 1, further comprising:
   a mouth suction tube including a suction opening for removal of secretion and/or mucus from the mouth, adapted to extend from an external surface of the lengthy body at a location corresponding to a patient's mouth, wherein at least one longitudinal cavity of the plurality of discrete longitudinal cavities further comprising a mouth suction cavity continuous to the mouth suction tube; and
   a mouth suction outlet channel extending from the proximal end of the lengthy body, the mouth suction outlet channel is a continuous extension of the mouth suction cavity and configured to provide suction to the mouth suction cavity.

3. The add-on device of claim 2, the add-on device comprising a moisture sensor that senses dryness at a distal end of the mouth suction tube and at least one sensor data channel going through a core of thickness of the major arc-shaped cross section, and spaced apart from the plurality of discrete longitudinal cavities, towards the proximal end of the lengthy body.

4. The add-on device of claim 2, wherein the mouth suction tube is connected to the lengthy body by an axis perpendicular to the lengthy body at a connection point, the mouth suction tube tiltable about the axis to adjust the position of the mouth suction tube.

5. The add-on device of claim 2, further comprising:
   at least one impedance sensor for detection of liquid, disposed at the mouth suction tube, when in use corresponding to the patient's mouth;
   and at least one sensor data channel going through a core of thickness of the major arc-shaped cross section, and spaced apart from the plurality of discrete longitudinal cavities, towards the proximal end of the lengthy body.

6. The add-on device of claim 1, the add-on device comprising:
   a liquid outlet at an external surface of the lengthy body at a location corresponding to a patient's mouth, when in use;
   a longitudinal cavity comprising a liquid channel cavity continuous to the liquid outlet; and
   a liquid channel extending from the proximal end of the lengthy body, the liquid channel is a continuous extension of the liquid channel cavity and configured to provide liquid to the liquid outlet.

7. The add-on device of claim 6, wherein the liquid outlet is connected to the lengthy body by an axis perpendicular to the lengthy body at a connection point, the liquid outlet tiltable about the axis to adjust the position of the liquid outlet.

8. The add-on device of claim 1, comprising at the distal end of the lengthy body a recess formed in an internal wall of the lengthy body, configured to prevent clogging of a suction inlet.

9. The add-on device of claim 1, comprising an inlet at the distal end of the lengthy body and a $CO_2$ sampling pipe continuous to the inlet going through a longitudinal cavity towards the proximal end of the lengthy body.

10. The add-on device of claim 1, comprising an outlet bundle of outlet channels including the suction outlet channel, the outlet bundle extending from the proximal end of the lengthy body.

11. The add-on device of claim 1, wherein the plurality of discrete longitudinal cavities pass in a thickness of the lengthy body.

12. The add-on device of claim 1, wherein an outer surface across the length of the lengthy body is smooth.

13. The add-on device of claim 1, wherein the plurality of discrete longitudinal cavities are located within the major arc-shaped cross section, and passes along the length of the lengthy body.

14. The add-on device of claim 1, further comprising a liquid absorbing material disposed along two opposing sides of the longitudinal slit, wherein the liquid absorbing material is in an unexpanded state before the add-on device is installed over the ETT, keeping the longitudinal slit open for facilitating installation over the ETT while the ETT is located within the trachea of the ventilated patient, and wherein the liquid absorbing material absorbs fluids and expands to fill the longitudinal slit for gripping the add-on device to the ETT when the add-on device is installed over the ETT while the ETT is located within the trachea.

15. The add-on device of claim 1, wherein the controller automatically activates the suction as long as a predetermined condition is fulfilled.

16. The add-on device of claim 1, wherein the at least one impedance sensor is disposed within the core of thickness of a rim.

17. The add-on device of claim 1, wherein the at least one impedance sensor comprises a plurality of impedance sensors which are arranged alternating with the plurality of discrete longitudinal cavities along the core of thickness of the major arc-shaped cross section.

18. The add-on device of claim 1, further comprising a recess formed in the core of thickness of the major arc-shaped cross section, the recess in communication with the suction cavity.

19. The add-on device of claim 1, wherein the at least one impedance sensor is disposed at a rim of the distal end of the lengthy body.

20. The add-on device of claim 1, wherein the suction cavity ends with a suction inlet at the distal end of the lengthy body.

21. The add-on device of claim 1, wherein a plurality of sensor data channels and a plurality of suction cavities are arranged along a circumference of the core of thickness of the major arc-shaped cross section for coverage of the circumference for detection of liquid and suction of the liquid.

22. The add-on device of claim 1, wherein the distal end of the lengthy body is tapered, and the at least one impedance sensor is disposed on a tapered portion of the distal end.

23. The add-on device of claim 1, wherein the at least one impedance sensor is forward facing along a long axis of the add-on device, and disposed within the core of thickness of a rim.

24. An add-on device for an Endo-Tracheal Tube (ETT), the add-on device comprising:
    a liquid outlet at a location corresponding to a patient's mouth, when in use;
    a moisture sensor that senses dryness at a location corresponding to a patient's mouth, when in use;
    at least one longitudinal cavity passing within a lengthy body of the add-on device, wherein a major arc-shaped cross section extends along a length of the lengthy body, from a distal end of the lengthy body to a proximal end of the lengthy body, and comprising:
        a liquid channel cavity continuous to the liquid outlet; and
        a moisture sensor data channel, the liquid channel cavity and moisture sensor data channel going through the at least one longitudinal cavity towards a proximal end of the add-on device,
        wherein the liquid channel cavity is adapted to guide liquid from the a liquid source to the liquid outlet according to data transmitted through the moisture sensor data channel; and
    a controller that activates according to a data indicative of dryness sensed by the moisture sensor, a liquid source for providing liquid to the liquid outlet via the liquid channel cavity.

25. A system comprising:
    an add-on device for an Endo-Tracheal Tube (ETT), the add-on device comprising:
    a plurality of discrete longitudinal cavities each having an arc-shaped cross section passing within a lengthy body of the add-on device, wherein a major arc-shaped cross section extends along a length of the lengthy body, from a distal end of the lengthy body to a proximal end of the lengthy body, the lengthy body having a curvature and a longitudinal slit, the lengthy body comprising a suction cavity, the lengthy body sized and shaped for facilitating installation over the ETT while the ETT is located within a trachea of a ventilated patient;
    a suction outlet channel extending from a proximal end of the add-on device, the suction outlet channel is a continuous extension of the suction cavity and configured to provide suction to the suction cavity;
    at least one impedance sensor for detection of liquid, disposed at the distal end of the lengthy body;
    at least one sensor data channel from the at least one impedance sensor to the proximal end of the lengthy body, passing within a core of thickness of the major arc-shaped cross section, and spaced apart from the plurality of discrete longitudinal cavities; and
    a controller that receives data from the at least one impedance sensor and automatically activates suction of the suction outlet channel to create suction in the suction cavity when excessive wetness exceeding a pre-determined threshold is detected by the at least one impedance sensor
    a hub for operating the add-on device, the hub comprises the controller.

26. The system of claim 25, wherein the controller is configured to:
    detect excessive wetness based on moisture sensor data; and
    when excessive wetness is detected, activate suction through the suction outlet channel.

27. The system of claim 25, wherein the add-on device comprises:
    a mouth suction tube adapted to extend from an external surface of the add-on device at a location corresponding to a patient's mouth, wherein at least one longitudinal cavity of the plurality of discrete longitudinal cavities further comprising a mouth suction cavity continuous to the mouth suction tube; and
    a mouth suction outlet channel extending from the proximal end of the add-on device, the mouth suction outlet channel is a continuous extension of the mouth suction cavity and configured to provide suction to the mouth suction cavity,
    wherein the controller is configured to:
    switch a selection valve to select between the suction outlet channel and the mouth suction outlet channel; and
    switch a pinch valve to control suction supply to the selected suction outlet channel.

28. The system of claim 25, wherein the add-on device comprises:
    a liquid outlet at an external surface of the add-on device at a location corresponding to a patient's mouth, when in use;
    a longitudinal cavity comprising a liquid channel cavity continuous to the liquid outlet; and
    a liquid channel extending from the proximal end of the add-on device, the liquid channel is a continuous extension of the liquid channel cavity and configured to provide liquid to the liquid outlet,
    wherein the controller is configured to activate a liquid source to provide liquid via the liquid channel.

29. The system of claim 28, wherein the hub comprises an air compressor, wherein the controller is configured to activate the air compressor to push liquid forcefully through the liquid channel.

30. The system of claim 25, wherein the add-on device comprises an inlet at a distal end of the add-on device and a $CO_2$ sampling pipe continuous to the inlet going through a longitudinal cavity towards the proximal end of the add-on device, and wherein the hub comprises a $CO_2$ level sensor configured to receive a sample of air via the $CO_2$ sampling pipe and to measure $CO_2$ level in the sample.

31. The system of claim 30, wherein the controller is configured to detect air leakage based on the measured $CO_2$ level.

32. The system of claim 25, wherein the controller is configured to control inflation of an inflatable section of the ETT based on sensor data.

33. A method for controlling an add-on device for an Endo-Tracheal Tube (ETT), the method comprising:
    installing the add-on device over the ETT while the ETT is located within a trachea of a ventilated patient, by placing a lengthy body having a curvature, a major arc-shaped cross section and a longitudinal slit, the lengthy body sized and shaped for facilitating installation over the ETT while the ETT is located within the trachea of the ventilated patient, wherein the major arc-shaped cross section extends along a length of the lengthy body, from a distal end of the lengthy body to a proximal end of the lengthy body;

when the add-on device is installed on the ETT, sensing moisture at a distal end of the add-on device by at least one impedance sensor for detection of liquid disposed at the distal end of the lengthy body, wherein at least one sensor data channel from the at least one impedance sensor to the proximal end of the lengthy body, passes within a core of thickness of the major arc-shaped cross section, and spaced apart from a plurality of discrete longitudinal cavities; and in case of detection of excessive wetness, provide suction through a cavity of the plurality of discrete longitudinal cavities each having an arc-shaped cross section passing along the add-on device, the suction is provided via a suction outlet channel extending from a proximal end of the add-on device.

\* \* \* \* \*